US007763210B2

(12) United States Patent
Bedingham et al.

(10) Patent No.: US 7,763,210 B2
(45) Date of Patent: Jul. 27, 2010

(54) COMPLIANT MICROFLUIDIC SAMPLE PROCESSING DISKS

(75) Inventors: William Bedingham, Woodbury, MN (US); Barry W. Robole, Woodville, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 1069 days.

(21) Appl. No.: 11/174,680

(22) Filed: Jul. 5, 2005

(65) Prior Publication Data

US 2007/0009391 A1 Jan. 11, 2007

(51) Int. Cl.
*G01N 33/00* (2006.01)

(52) U.S. Cl. ......................... 422/100; 422/99; 422/68.1

(58) Field of Classification Search ................. 422/100, 422/99, 68.1
See application file for complete search history.

(56) References Cited

U.S. PATENT DOCUMENTS 3,555,284 A 1/1971 Anderson
3,795,451 A 3/1974 Mailen
3,798,459 A 3/1974 Anderson et al.
3,856,470 A 12/1974 Cullis et al.
3,873,217 A 3/1975 Anderson et al.
3,912,799 A 10/1975 Chisholm
3,964,867 A 6/1976 Berry
4,030,834 A 6/1977 Bauer et al.
4,111,304 A 9/1978 Lucas
4,123,173 A 10/1978 Bullock et al.
4,244,916 A 1/1981 Guigan
4,252,538 A 2/1981 Barr
4,256,696 A 3/1981 Soodak
4,384,193 A 5/1983 Kledzik et al.
4,390,499 A 6/1983 Curtis et al.
4,396,579 A 8/1983 Schroeder et al. ............. 422/52
D271,993 S 12/1983 Swartz ........................ D24/17
4,456,581 A 6/1984 Edelmann et al.

(Continued)

FOREIGN PATENT DOCUMENTS

CA 2 130 013 3/1999

(Continued)

OTHER PUBLICATIONS

U.S. Appl. No. 29/233,477, filed Jul. 5, 2005, Bedingham et al.

(Continued)

*Primary Examiner*—Sam P Siefke
(74) *Attorney, Agent, or Firm*—Nicole J. Einerson

(57) ABSTRACT

Microfluidic sample processing disks with a plurality of fluid structures formed therein are disclosed. Each of the fluid structures preferably includes an input well and one or more process chambers connected to the input well by one or more delivery channels. The process chambers may be arranged in a compliant annular processing ring that is adapted to conform to the shape of an underlying thermal transfer surface under pressure. That compliance may be delivered in the disks of the present invention by locating the process chambers in an annular processing ring in which a majority of the volume is occupied by the process chambers. Compliance within the annular processing ring may alternatively be provided by a composite structure within the annular processing ring that includes covers attached to a body using pressure sensitive adhesive.

31 Claims, 3 Drawing Sheets

U.S. PATENT DOCUMENTS

D274,553 S 7/1984 Perry .......................... D24/17
4,476,733 A 10/1984 Chlosta et al.
4,488,810 A 12/1984 Hatanaka et al.
4,498,896 A 2/1985 Leis
D277,891 S 3/1985 Uffenheimer et al. ........ D24/31
4,554,436 A 11/1985 Chlosta et al.
4,580,896 A 4/1986 Brickus et al. .............. 356/246
4,632,908 A 12/1986 Schultz
D288,124 S 2/1987 Brickus et al. ............... D24/31
4,673,657 A 6/1987 Christian
4,695,430 A 9/1987 Coville et al.
4,814,279 A 3/1989 Sugaya
4,906,432 A 3/1990 Geiselman
4,933,146 A 6/1990 Meyer et al.
4,981,801 A 1/1991 Suzuki et al.
5,086,337 A 2/1992 Noro et al. .................... 357/79
D329,024 S 9/1992 Marks ......................... D10/80
5,154,888 A 10/1992 Zander et al.
5,182,083 A 1/1993 Barker et al.
5,207,987 A 5/1993 Kureshy et al.
5,219,526 A 6/1993 Long
5,229,297 A 7/1993 Schnipelsky et al.
5,254,479 A 10/1993 Chemelli
5,258,163 A 11/1993 Krause et al.
5,264,184 A 11/1993 Aysta et al.
5,278,377 A 1/1994 Tsai
5,288,463 A 2/1994 Chemelli
5,310,523 A 5/1994 Smethers et al.
5,336,467 A 8/1994 Heidt et al.
5,411,065 A 5/1995 Meador et al.
5,415,839 A 5/1995 Zaun et al.
5,422,271 A 6/1995 Chen et al.
5,439,649 A 8/1995 Tseung et al.
5,446,270 A 8/1995 Chamberlain et al.
5,461,134 A 10/1995 Leir et al.
5,464,541 A 11/1995 Aysta et al.
5,496,518 A 3/1996 Arai et al. ..................... 422/64
5,496,520 A 3/1996 Kelton et al.
5,527,931 A 6/1996 Rich et al. .................. 556/413
5,529,708 A 6/1996 Palmgren et al.
5,571,410 A 11/1996 Swedberg et al.
5,587,128 A 12/1996 Wilding et al.
5,593,838 A 1/1997 Zanzucchi et al.
5,599,501 A 2/1997 Carey et al.
5,601,141 A 2/1997 Gordon et al.
5,604,130 A 2/1997 Warner et al.
5,616,301 A 4/1997 Moser et al.
5,637,469 A 6/1997 Wilding et al.
5,639,428 A 6/1997 Cottingham
5,691,208 A 11/1997 Miltenyi et al.
RE35,716 E 1/1998 Stapleton et al.
5,720,923 A 2/1998 Haff et al.
5,721,123 A 2/1998 Hayes et al.
5,726,026 A 3/1998 Wilding et al.
5,792,372 A 8/1998 Brown et al.
5,795,547 A 8/1998 Moser et al.
5,800,785 A 9/1998 Bochner
5,804,141 A 9/1998 Chianese
5,811,296 A 9/1998 Chemelli et al.
5,819,842 A 10/1998 Potter et al.
5,833,923 A 11/1998 McClintock et al.
5,863,502 A 1/1999 Southgate et al.
5,863,801 A 1/1999 Southgate et al.
5,869,002 A 2/1999 Limon et al.
5,876,675 A 3/1999 Kennedy
5,886,863 A 3/1999 Nagasaki et al.
5,922,617 A 7/1999 Wang et al.
5,925,455 A 7/1999 Bruzzone et al.
6,001,643 A 12/1999 Spaulding ................... 435/298
6,007,914 A 12/1999 Joseph et al.
6,013,513 A 1/2000 Reber et al.
6,030,581 A 2/2000 Virtanen
6,048,457 A 4/2000 Kopaciewicz et al.
6,063,589 A 5/2000 Kellogg et al.
6,068,751 A 5/2000 Neukermans
6,093,370 A 7/2000 Yasuda et al.
6,103,199 A 8/2000 Bjornson et al.
6,143,248 A 11/2000 Kellogg et al.
6,153,012 A 11/2000 Rupp et al.
6,168,759 B1 1/2001 Green et al.
6,183,693 B1 2/2001 Bogen et al.
6,184,029 B1 2/2001 Wilding et al.
6,190,617 B1 2/2001 Clark et al.
6,197,595 B1 3/2001 Anderson et al.
D441,873 S 5/2001 Köhler ...................... D24/219
6,284,113 B1 9/2001 Bjornson et al.
6,296,809 B1 10/2001 Richards et al.
6,302,134 B1 10/2001 Kellogg et al.
6,319,469 B1 11/2001 Mian et al.
6,344,326 B1 2/2002 Nelson et al.
6,375,898 B1 4/2002 Ulrich et al.
6,391,264 B2 5/2002 Hammer et al.
6,399,025 B1 6/2002 Chow
6,413,782 B1 7/2002 Parce et al.
6,432,635 B1 8/2002 Levin et al.
6,461,287 B1 10/2002 Glater
6,465,225 B1 10/2002 Fuhr et al.
6,467,275 B1 10/2002 Ghoshal
6,527,432 B2 3/2003 Kellogg et al.
6,532,997 B1 3/2003 Bedingham et al.
6,548,788 B2 4/2003 Kellogg et al.
6,558,947 B1 5/2003 Lund et al.
6,566,637 B1 5/2003 Revesz et al.
6,572,830 B1 6/2003 Burdon et al.
6,582,662 B1 6/2003 Kellogg et al.
6,593,143 B1 7/2003 Gordon
6,617,136 B2 9/2003 Parthasarathy et al.
6,627,159 B1 9/2003 Bedingham et al.
6,632,399 B1 10/2003 Kellogg et al.
6,645,758 B1 11/2003 Schnipelsky et al.
6,660,147 B1 12/2003 Woudenberg et al.
6,664,104 B2 12/2003 Pourahmadi et al.
6,720,187 B2 4/2004 Bedingham et al.
6,730,516 B2 5/2004 Jedrzejewski et al.
6,734,401 B2 5/2004 Bedingham et al.
6,814,935 B2 11/2004 Harms et al.
6,824,738 B1 11/2004 Neeper et al. ................. 422/72
6,889,468 B2 5/2005 Bedingham et al.
6,987,253 B2 1/2006 Bedingham et al.
7,026,168 B2 4/2006 Bedingham et al.
7,164,107 B2 1/2007 Bedingham et al.
7,192,560 B2 * 3/2007 Parthasarathy et al. ...... 422/101
7,273,591 B2 9/2007 Sellers et al.
7,322,254 B2 1/2008 Bedingham et al.
D564,667 S 3/2008 Bedingham et al. ........ D24/216
7,396,508 B1 7/2008 Richards et al.
7,569,186 B2 8/2009 Bedingham et al.
2002/0047003 A1 4/2002 Bedingham et al.
2002/0048533 A1 4/2002 Harms et al.
2002/0064885 A1 5/2002 Bedingham et al.
2003/0013203 A1 1/2003 Jedrzejewski et al.
2003/0044322 A1 3/2003 Andersson et al.
2003/0053934 A1 3/2003 Andersson et al.
2003/0118804 A1 6/2003 Bedingham et al. ......... 428/301
2003/0124506 A1 7/2003 Bedingham et al.
2003/0138779 A1 7/2003 Parthasarathy et al.
2003/0152491 A1 8/2003 Kellogg et al.
2003/0152994 A1 8/2003 Woudenberg et al.
2003/0231878 A1 12/2003 Shigeura
2004/0016898 A1 1/2004 Cox et al.
2004/0018116 A1 1/2004 Desmond et al.
2004/0018117 A1 1/2004 Desmond et al.
2004/0023371 A1 2/2004 Fawcett
2004/0121471 A1 6/2004 Dufresne et al.

| | | | |
|---|---|---|---|
| 2004/0179974 A1 | 9/2004 | Bedingham et al. | |
| 2005/0036911 A1 | 2/2005 | Sellers et al. | |
| 2005/0130177 A1 | 6/2005 | Bedingham et al. | |
| 2005/0142663 A1 | 6/2005 | Parthasarathy et al. | |
| 2005/0180890 A1 | 8/2005 | Bedingham et al. | |
| 2006/0013732 A1 | 1/2006 | Parthasarathy et al. | |
| 2006/0269451 A1 | 11/2006 | Bedingham et al. | |
| 2007/0007270 A1 | 1/2007 | Bedingham et al. | |
| 2007/0010007 A1 | 1/2007 | Ayasta et al. | |
| 2007/0114229 A1 | 5/2007 | Bedingham et al. | |
| 2007/0142780 A1 | 6/2007 | Van Lue | 604/167 |

FOREIGN PATENT DOCUMENTS

| | | | |
|---|---|---|---|
| DE | 3712624 | | 11/1988 |
| EP | 0 169 306 | A2 | 1/1986 |
| EP | 0 169 306 | B1 | 5/1990 |
| EP | 0 402 994 | A2 | 12/1990 |
| EP | 0 402 994 | B1 | 11/1994 |
| EP | 0 693 560 | A2 | 1/1996 |
| EP | 0 807 468 | A2 | 11/1997 |
| EP | 0 807 486 | A2 | 11/1997 |
| EP | 0 807 486 | A3 | 11/1997 |
| EP | 0 810 030 | A1 | 12/1997 |
| EP | 0 965 388 | | 12/1999 |
| EP | 1 010 979 | A1 | 6/2000 |
| EP | 0 807 486 | B1 | 12/2001 |
| EP | 0 810 030 | B1 | 3/2003 |
| EP | 1 010 979 | B1 | 10/2003 |
| JP | 9-72912 | | 3/1997 |
| JP | 11124419 | | 5/1999 |
| WO | WO 91/19567 | A1 | 12/1991 |
| WO | WO 94/26414 | A1 | 11/1994 |
| WO | WO 94/29400 | A1 | 12/1994 |
| WO | WO 95/18676 | A1 | 7/1995 |
| WO | WO 96/15576 | A1 | 5/1996 |
| WO | WO 96/34028 | A1 | 10/1996 |
| WO | WO 96/34029 | A1 | 10/1996 |
| WO | WO 96/35458 | A2 | 11/1996 |
| WO | WO 96/41864 | A1 | 12/1996 |
| WO | WO 97/00230 | | 1/1997 |
| WO | WO 97/21090 | A1 | 6/1997 |
| WO | WO 97/46707 | A2 | 12/1997 |
| WO | WO 97/46707 | A3 | 12/1997 |
| WO | WO 98/07019 | A1 | 2/1998 |
| WO | WO 98/49340 | A1 | 11/1998 |
| WO | WO 98/50147 | A1 | 11/1998 |
| WO | WO 98/53311 | A2 | 11/1998 |
| WO | WO 99/09394 | A1 | 2/1999 |
| WO | WO 99/44740 | A1 | 9/1999 |
| WO | WO 99/55827 | A1 | 11/1999 |
| WO | WO 99/58245 | A1 | 11/1999 |
| WO | WO 99/67639 | A1 | 12/1999 |
| WO | WO 00/05582 | A2 | 2/2000 |
| WO | WO 00/40750 | A1 | 7/2000 |
| WO | WO 00/45180 | | 8/2000 |
| WO | WO 00/50172 | A1 | 8/2000 |
| WO | WO 00/50642 | A1 | 8/2000 |
| WO | WO 00/68336 | A1 | 11/2000 |
| WO | WO 00/69560 | A1 | 11/2000 |
| WO | WO 00/78455 | A1 | 12/2000 |
| WO | WO 00/79285 | A2 | 12/2000 |
| WO | 01/12327 | | 2/2001 |
| WO | WO 01/07892 | A1 | 2/2001 |
| WO | 01/30995 | | 5/2001 |
| WO | 03/054509 | | 7/2003 |
| WO | 03/054510 | | 7/2003 |
| WO | 03/058224 | | 7/2003 |
| WO | WO 03/058253 | A1 | 7/2003 |
| WO | WO 03/104783 | A1 | 12/2003 |
| WO | 2004/010760 | | 2/2004 |
| WO | WO 2004/011143 | A2 | 2/2004 |
| WO | WO 2004/011147 | A1 | 2/2004 |
| WO | WO 2004/011148 | A2 | 2/2004 |
| WO | WO 2004/011149 | A1 | 2/2004 |
| WO | WO 2004/011365 | A2 | 2/2004 |
| WO | WO 2004/011592 | A2 | 2/2004 |
| WO | WO 2004/011681 | A1 | 2/2004 |
| WO | 2004/094672 | | 11/2004 |
| WO | WO 2005/005045 | A1 | 1/2005 |
| WO | WO 2005/016532 | A2 | 2/2005 |
| WO | WO 2005/016532 | A3 | 2/2005 |

OTHER PUBLICATIONS

*Handbook of Pressure Sensitive Adhesive Technology*, Donatas Satas (Ed.) 2nd Edition, Title page, Publication page, Table of Contents, and p. 172, and Fig. 8-16 on p. 173, Van Nostrand Reinhold, New York, NY 1989.

*Handbook of Pressure Sensitive Adhesive Technology*, 3rd Edition, Title page, Publication page, Table of Contents, and pp. 508-517.

Litton Product Brochure; Poly Scientific EC3848 High Speed Slip Ring Capsule; Blacksburg, VA; 2 pgs (Oct. 1999).

Meridian Laboratory Datasheet [online]; Rotocon high performance rotary electrical contacts; 5 pgs [retrieved on Jun. 18, 2002]. Retrieved from the Internet: <http://www.meridianlab.com/>.

Meridian Laboratory Datasheet [online]: Model MM Micro-Minature; 5 pgs. [retrieved on Jul. 19, 2001]. Retrieved from the Internet: <http://www.meridianlab.com/mm.htm>.

Motion Technology Product Guide; Commercial and Military/Aerospace Applications; Blacksburg, VA; 8 pgs. (Jul. 1999).

NIST Grant, Project Brief [online]; "Tools for DNA Diagnostics (Oct. 1998) Integrated, Micro-Sample Preparation System for Genetic Analysis," [retrieved on Aug. 5, 2002] 2 pgs. Retrieved form the internet at <http://jazz.nist.gov/atpcf/prjbriefs/prjbrief.cfm?ProjectNumber=98-08-0031>.

*Test Methods for Pressure Sensitive Adhesive Tapes*, Pressure Sensitive Tape Council, (1996) (4 pgs).

* cited by examiner

COMPLIANT MICROFLUIDIC SAMPLE PROCESSING DISKS

The present invention relates to the field of microfluidic sample processing disks used to process samples that may contain one or more analytes of interest.

Many different chemical, biochemical, and other reactions are sensitive to temperature variations. Examples of thermal processes in the area of genetic amplification include, but are not limited to, Polymerase Chain Reaction (PCR), Sanger sequencing, etc. The reactions may be enhanced or inhibited based on the temperatures of the materials involved. Although it may be possible to process samples individually and obtain accurate sample-to-sample results, individual processing can be time-consuming and expensive.

One approach to reducing the time and cost of thermally processing multiple samples is to use a device including multiple chambers in which different portions of one sample or different samples can be processed simultaneously. When multiple reactions are performed in different chambers, however, one significant problem can be accurate control of chamber-to-chamber temperature uniformity. Temperature variations between chambers may result in misleading or inaccurate results. In some reactions, for example, it may be critical to control chamber-to-chamber temperatures within the range of ±1° C. or less to obtain accurate results.

The need for accurate temperature control may manifest itself as the need to maintain a desired temperature in each of the chambers, or it may involve a change in temperature, e.g., raising or lowering the temperature in each of the chambers to a desired setpoint. In reactions involving a change in temperature, the speed or rate at which the temperature changes in each of the chambers may also pose a problem. For example, slow temperature transitions may be problematic if unwanted side reactions occur at intermediate temperatures. Alternatively, temperature transitions that are too rapid may cause other problems. As a result, another problem that may be encountered is comparable chamber-to-chamber temperature transition rate.

In addition to chamber-to-chamber temperature uniformity and comparable chamber-to-chamber temperature transition rate, another problem may be encountered in those reactions in which thermal cycling is required is overall speed of the entire process. For example, multiple transitions between upper and lower temperatures may be required. Alternatively, a variety of transitions (upward and/or downward) between three or more desired temperatures may be required. In some reactions, e.g., polymerase chain reaction (PCR), thermal cycling must be repeated up to thirty or more times. Thermal cycling devices and methods that attempt to address the problems of chamber-to-chamber temperature uniformity and comparable chamber-to-chamber temperature transition rates, however, typically suffer from a lack of overall speed—resulting in extended processing times that ultimately raise the cost of the procedures.

One or more of the above problems may be implicated in a variety of chemical, biochemical and other processes. Examples of some reactions that may require accurate chamber-to-chamber temperature control, comparable temperature transition rates, and/or rapid transitions between temperatures include, e.g., the manipulation of nucleic acid samples to assist in the deciphering of the genetic code. Nucleic acid manipulation techniques include amplification methods such as polymerase chain reaction (PCR); target polynucleotide amplification methods such as self-sustained sequence replication (3SR) and strand-displacement amplification (SDA); methods based on amplification of a signal attached to the target polynucleotide, such as "branched chain" DNA amplification; methods based on amplification of probe DNA, such as ligase chain reaction (LCR) and QB replicase amplification (QBR); transcription-based methods, such as ligation activated transcription (LAT) and nucleic acid sequence-based amplification (NASBA); and various other amplification methods, such as repair chain reaction (RCR) and cycling probe reaction (CPR). Other examples of nucleic acid manipulation techniques include, e.g., Sanger sequencing, ligand-binding assays, etc.

One common example of a reaction in which all of the problems discussed above may be implicated is PCR amplification. Traditional thermal cycling equipment for conducting PCR uses polymeric microcuvettes that are individually inserted into bores in a metal block. The sample temperatures are then cycled between low and high temperatures, e.g., 55° C. and 95° C. for PCR processes. When using the traditional equipment according to the traditional methods, the high thermal mass of the thermal cycling equipment (which typically includes the metal block and a heated cover block) and the relatively low thermal conductivity of the polymeric materials used for the microcuvettes result in processes that can require two, three, or more hours to complete for a typical PCR amplification.

One attempt at addressing the relatively long thermal cycling times in PCR amplification involves the use of a device integrating 96 microwells and distribution channels on a single polymeric card. Integrating 96 microwells in a single card does address the issues related to individually loading each sample cuvette into the thermal block. This approach does not, however, address the thermal cycling issues such as the high thermal mass of the metal block and heated cover or the relatively low thermal conductivity of the polymeric materials used to form the card. In addition, the thermal mass of the integrating card structure can extend thermal cycling times. Another potential problem of this approach is that if the card containing the sample wells is not seated precisely on the metal block, uneven well-to-well temperatures can be experienced, causing inaccurate test results.

Yet another problem that may be experienced in many of these approaches is that the volume of sample material may be limited and/or the cost of the reagents to be used in connection with the sample materials may also be limited and/or expensive. As a result, there is a desire to use small volumes of sample materials and associated reagents. When using small volumes of these materials, however, additional problems related to the loss of sample material and/or reagent volume through vaporization, etc. may be experienced as the sample materials are, e.g., thermally cycled.

Another problem that may be experienced in the preparation of finished samples (e.g., isolated or purified samples of, e.g., nucleic acid materials such as DNA, RNA, etc.) of human, animal, plant, or bacterial origin from raw sample materials (e.g., blood, tissue, etc.) is the number of thermal processing steps and other methods that must be performed to obtain the desired end product (e.g., purified nucleic acid materials). In some cases, a number of different thermal processes must be performed, in addition to filtering and other process steps, to obtain the desired finished samples. In addition to suffering from the thermal control problems discussed above, all or some of these processes may require the attention of highly skilled professionals and/or expensive equipment. In addition, the time required to complete all of the different process steps may be days or weeks depending on the availability of personnel and/or equipment.

SUMMARY OF THE INVENTION

The present invention provides a microfluidic sample processing disk with a plurality of fluid structures formed therein. Each of the fluid structures preferably includes an input well and one or more process chambers connected to the input well by one or more delivery channels.

One potential advantage of some of the microfluidic sample processing disks of the present invention may include, e.g., process chambers arranged in a compliant annular processing ring that is adapted to conform to the shape of an underlying thermal transfer surface under pressure. That compliance may be delivered in the disks of the present invention by, e.g., locating the process chambers in an annular processing ring in which a majority of the volume is occupied by the process chambers which are preferably formed by voids extending through the body of the disks. In such a construction, limited amounts of the body forming the structure of the disk are present within the annular processing ring, resulting in improved flexibility of the disk within the annular processing ring. Further compliance and flexibility may be achieved by locating orphan chambers within the annular processing ring, the orphan chambers further reducing the amount of body material present in the annular processing ring.

Other optional features that may improve compliance within the annular processing ring may include a composite structure within the annular processing ring that includes covers attached to a body using pressure sensitive adhesive that exhibits viscoelastic properties. The viscoelastic properties of pressure sensitive adhesives may allow for relative movement of the covers and bodies during deformation or thermal expansion/contraction while maintaining fluidic integrity of the fluid structures in the sample processing disks of the present invention.

The use of covers attached to a body as described in connection with the sample processing disks of the present invention may also provide advantages in that the properties of the materials for the different covers and bodies may be selected to enhance performance of the disk.

For example, some of the covers may preferably be constructed of relatively inextensible materials to resist bulging or deformation in response forces generated by the sample materials within the process chambers and other features of the fluid structures. Those forces may be significant where, e.g., the sample processing disk is rotated to deliver and/or process sample materials in the process chambers. Examples of some materials that may be relatively inextensible may include, e.g., polyesters, metal foils, polycarbonates, etc. It should, however, be understood that inextensibility may not necessarily be required. For example, in some embodiments, one or more covers may be selected because they provide for some extensibility.

Another property that may preferably be exhibited by some of the covers used in connection with the present invention is thermal conductivity. Using materials for the covers that enhance thermal conductivity may improve thermal performance where, e.g., the temperature of the sample materials in the process chambers are preferably heated or cooled rapidly to selected temperatures or where close temperature control is desirable. Examples of materials that may provide desirable thermal conductive properties may include, e.g., metallic layers (e.g., metallic foils), thin polymeric layers, etc.

Another potentially useful property in the covers used in connection with the present invention may be their ability to transmit electromagnetic energy of selected wavelengths. For example, in some disks, electromagnetic energy may be delivered into the process chambers to heat materials, excite materials (that may, e.g., fluoresce, etc.), visually monitor the materials in the process chamber, etc.

As discussed above, if the materials used for the covers are too extensible, they may bulge or otherwise distort at undesirable levels during, e.g., rotation of the disk, heating of materials within the process chambers, etc. One potentially desirable combination of properties in the covers used to construct process chambers of the present invention may include relative inextensibility, transmissivity to electromagnetic energy of selected wavelengths, and thermal conductivity. Where each process chamber is constructed by a void in the central body and a pair of covers on each side, one cover may be selected to provide the desired transmissivity and inextensibility while the other cover may be selected to provide thermal conductivity and inextensibility. One suitable combination of covers may include, e.g., a polyester cover that provides transmissivity and relative inextensibility and a metallic foil cover that provides thermal conductivity and inextensibility on the opposite side of the process chamber. Using pressure sensitive adhesive to attach relatively inextensible covers to the body of the disks may preferably improve compliance and flexibility by allowing relative movement between the covers and the body that may not be present in other constructions.

The microfluidic sample processing disks of the present invention are designed for processing sample materials that include chemical and/or biological mixtures with at least a portion being in the form of a liquid component. If the sample materials include a biological mixture, the biological mixture may preferably include biological material such as peptide- and/or nucleotide-containing material. It may further be preferred that the biological mixture include a nucleic acid amplification reaction mixture (e.g., a PCR reaction mixture or a nucleic acid sequencing reaction mixture).

Further, the fluid structures may preferably be unvented, such that the only opening into or out of the fluid structure is located proximate the input well into which the sample materials are introduced. In an unvented fluid structure, the terminal end, i.e., the portion distal from the axis of rotation and/or the input well, is sealed to prevent the exit of fluids from the process chamber.

Potential advantages of some of the microfluidic sample processing disks of the present invention may include, e.g., arrangements of unvented fluid structures in which the delivery channels and process chambers are arranged to promote fluid flow from the input wells to the process chambers as the disk is rotated about an axis (that is preferably perpendicular to the major surfaces of the disk). It may be preferred, for example, that the process chambers be rotationally offset from the input well feeding into them, such that at least a portion of the delivery channel follows a path that is not coincident with a radial line formed through the center of the disk (assuming that the axis of rotation extends through the center of the disk). The offset may place process chambers ahead or behind the input wells depending on the direction in which the disk is rotated. The movement of fluid through the delivery channels may be promoted in unvented fluid structures because the liquid will move along one side of the channel while air can pass along the opposite side. For example, the liquid sample mixture may preferentially follow the lagging side of the delivery channel during rotation while air being displaced from the process chamber by the liquid sample mixture moves along the leading side of the delivery channel from the process chamber to the input well.

In one aspect, the present invention provides a microfluidic sample processing disk that includes a body having first and second major surfaces; a plurality of fluid structures, wherein each fluid structure of the plurality of fluid structures includes an input well having an opening; a process chamber located radially outward of the input well, wherein the process chamber includes a void formed through the first and second major surfaces of the body; and a delivery channel connecting the input well to the process chamber, wherein the delivery channel includes an inner channel formed in the second major surface of the body, an outer channel formed in the first major surface of the body, and a via formed through the first and second major surfaces of the body, wherein the via connects the inner channel to the outer channel; wherein the vias and the process chambers of the plurality of fluid structures define annular rings on the body. The disk further includes a first annular cover attached to the first major surface of the body, the first annular cover defining the vias, the outer channels, and the process chambers in connection with the first major surface of the body; a second annular cover attached to the second major surface of the body, the second annular cover defining the process chambers of the plurality of fluid structures in connection with the second major surface of the body, wherein an inner edge of the second annular cover is located radially outward of the annular ring defined by the vias of the plurality of fluid structures; and a central cover attached to the second major surface of the body, the central cover defining the inner channels and the vias in connection with the second major surface of the body, wherein an outer edge of the central cover is located radially outward of the annular ring defined by the vias of the plurality of fluid structures.

In another aspect, the present invention provides a microfluidic sample processing disk that includes a body with first and second major surfaces; a plurality of fluid structures, wherein each fluid structure of the plurality of fluid structures includes an input well with an opening; a process chamber located radially outward of the input well, wherein the process chamber includes a void formed through the first and second major surfaces of the body; and a delivery channel connecting the input well to the process chamber. The disk also includes a first cover attached to the first major surface of the body with a pressure sensitive adhesive, the first cover defining a portion of the process chambers of the plurality of fluid structures in connection with the first major surface of the body; a second cover attached to the second major surface of the body with a pressure sensitive adhesive, the second cover defining a portion of the process chambers of the plurality of fluid structures in connection with the second major surface of the body, wherein the second cover has an inner edge and an outer edge that is located radially outward of the inner edge; wherein the process chambers of the plurality of fluid structures define an annular processing ring that includes an inner edge and an outer edge located radially inward of a perimeter of the body, wherein the inner edge of the annular processing ring is located radially outward of the inner edge of the second cover.

In another aspect, the present invention provides a microfluidic sample processing disk that includes a body with first and second major surfaces; an annular processing ring including a plurality of process chambers formed in the body, each process chamber of the plurality of process chambers defining an independent volume for containing sample material; an annular metallic layer located within the annular processing ring, wherein the annular metallic layer is proximate the first surface of the body, wherein the plurality of process chambers are located between the annular metallic layer and the second major surface of the body; a plurality of channels formed in the body, wherein each channel of the plurality of channels is in fluid communication with at least one process chamber of the plurality of process chambers; wherein the annular processing ring is a compliant structure in which the independent volumes of the plurality of process chambers maintain fluidic integrity when a portion of the annular processing ring is deflected in a direction normal to the first and second major surfaces of the body.

These and other features and advantages of various embodiments of the present invention may be discussed below in connection with various exemplary embodiments of the present invention.

BRIEF DESCRIPTIONS OF THE FIGURES

DESCRIPTION OF EXEMPLARY EMBODIMENTS OF THE INVENTION

Figure 1:
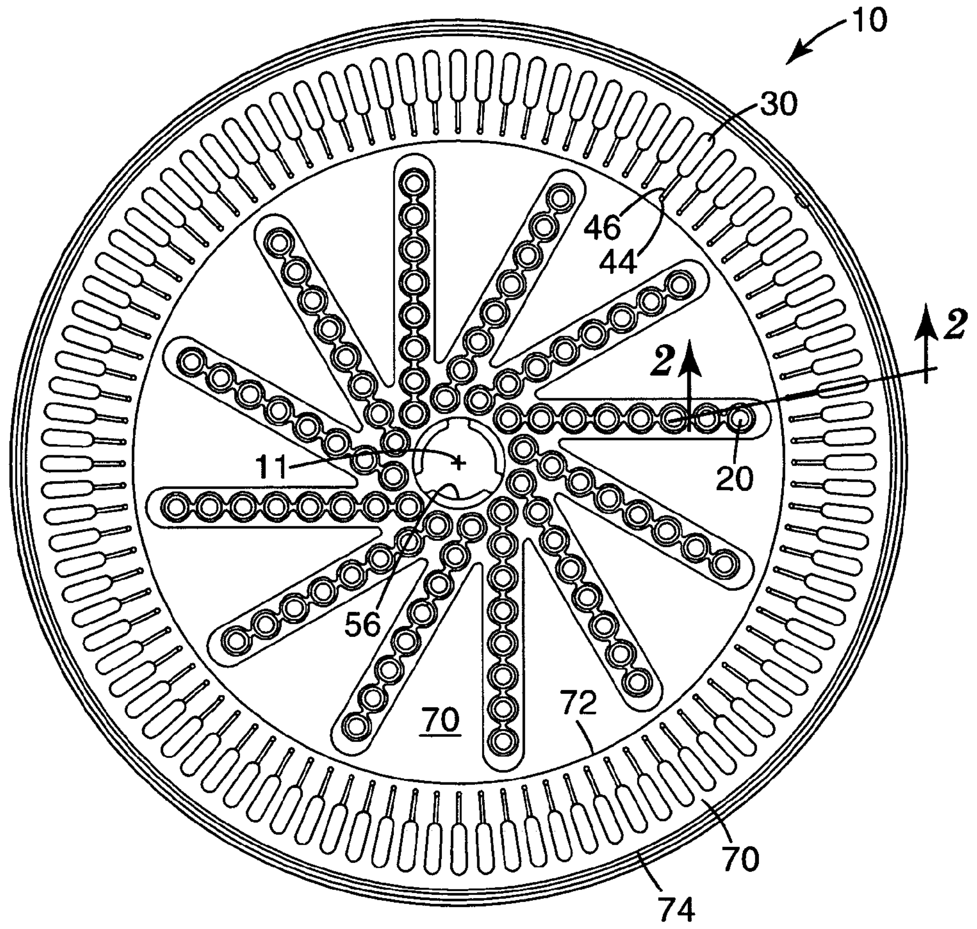
FIG. 1 is a plan view of one major surface of an exemplary embodiment of a microfluidic sample processing disk according to the present invention.

In the following description of exemplary embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the present invention.

The present invention provides microfluidic sample processing disks and methods for using them that involve thermal processing, e.g., sensitive chemical processes such as PCR amplification, ligase chain reaction (LCR), self-sustaining sequence replication, enzyme kinetic studies, homogeneous ligand binding assays, and more complex biochemical or other processes that require precise thermal control and/or rapid thermal variations. The sample processing disks are preferably capable of being rotated while the temperature of sample materials in process chambers in the disks is being controlled.

Some examples of suitable construction techniques/materials that may be used in connection with the disks and methods of the present invention may be described in, e.g., commonly-assigned U.S. Pat. No. 6,734,401 titled ENHANCED SAMPLE PROCESSING DEVICES SYSTEMS AND METHODS (Bedingham et al.) and U.S. Patent Application Publication No. US 2002/0064885 titled SAMPLE PROCESSING DEVICES. Other useable device constructions may be found in, e.g., U.S. Provisional Patent Application Ser. No. 60/214,508 filed on Jun. 28, 2000 and entitled THERMAL PROCESSING DEVICES AND METHODS;

U.S. Provisional Patent Application Ser. No. 60/214,642 filed on Jun. 28, 2000 and entitled SAMPLE PROCESSING DEVICES, SYSTEMS AND METHODS; U.S. Provisional Patent Application Ser. No. 60/237,072 filed on Oct. 2, 2000 and entitled SAMPLE PROCESSING DEVICES, SYSTEMS AND METHODS; U.S. Provisional Patent Application Ser. No. 60/260,063 filed on Jan. 6, 2001 and titled SAMPLE PROCESSING DEVICES, SYSTEMS AND METHODS; U.S. Provisional Patent Application Ser. No. 60/284,637 filed on Apr. 18, 2001 and titled ENHANCED SAMPLE PROCESSING DEVICES, SYSTEMS AND METHODS; and U.S. Patent Application Publication No. US 2002/0048533 titled SAMPLE PROCESSING DEVICES AND CARRIERS. Other potential device constructions may be found in, e.g., U.S. Pat. No. 6,627,159 titled CENTRIFUGAL FILLING OF SAMPLE PROCESSING DEVICES (Bedingham et al.).

Although relative positional terms such as "top", "bottom", "above", "below", etc. may be used in connection with the present invention, it should be understood that those terms are used in their relative sense only. For example, when used in connection with the devices of the present invention, "top" and "bottom" may be used to signify opposing major sides of the disks. In actual use, elements described as "top" or "bottom" may be found in any orientation or location and should not be considered as limiting the disks and methods to any particular orientation or location. For example, the top surface of the sample processing disk may actually be located below the bottom surface of the sample processing disk during processing (although the top surface would still be found on the opposite side of the sample processing disk from the bottom surface).

Figure 2:
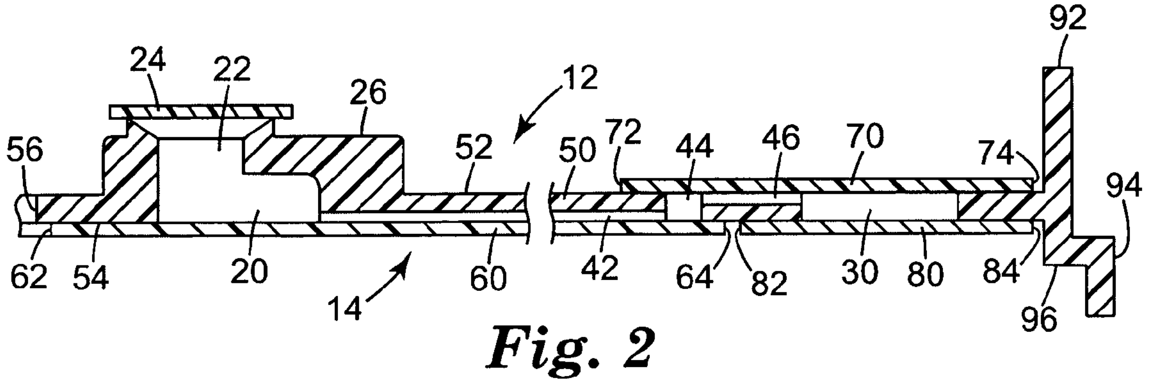
FIG. 2 is an enlarged cross-sectional view of one fluid structure in the disk of FIG. 1 taken along line 2-2 in FIG. 1.
Figure 3:
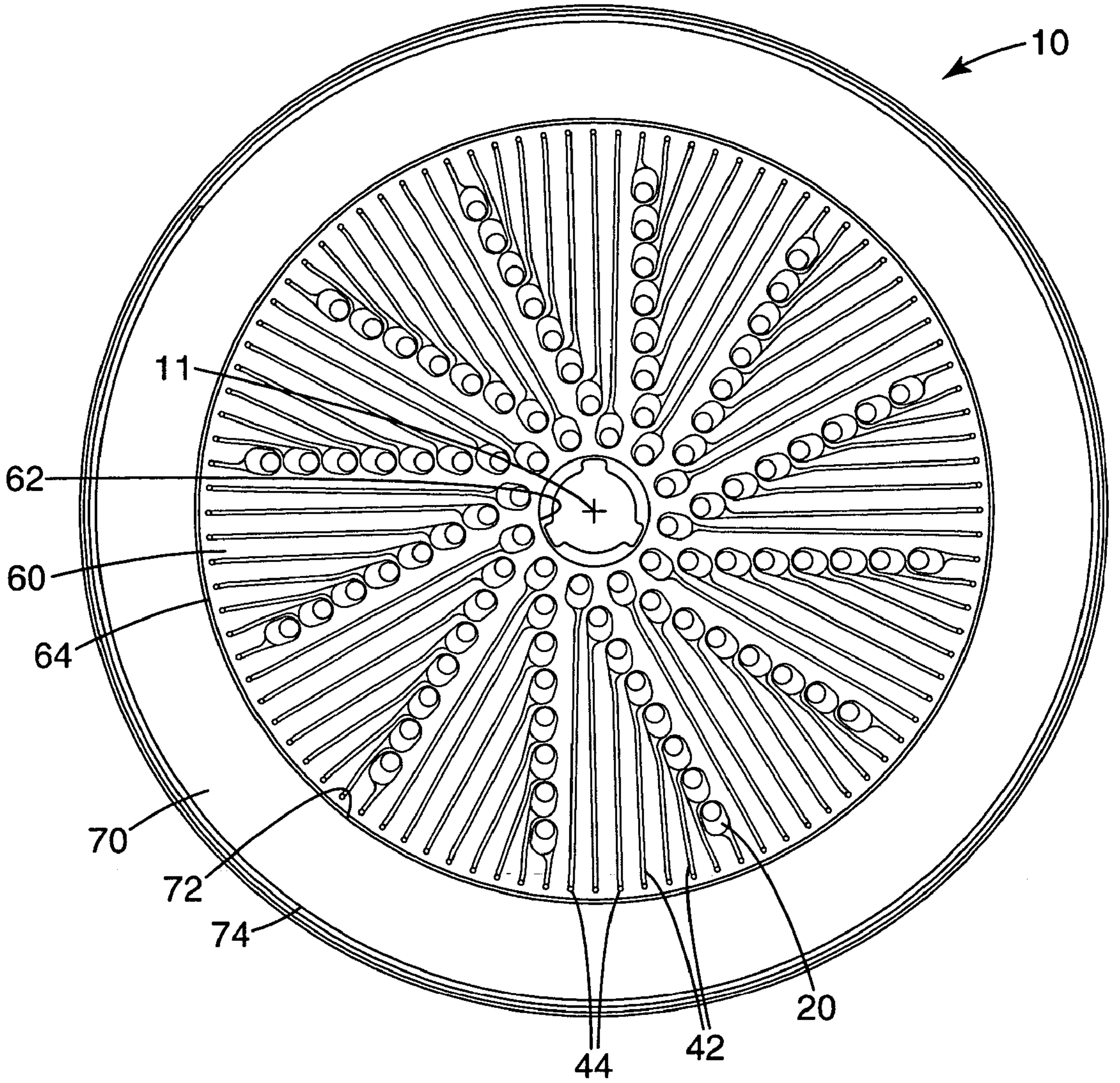
FIG. 3 is a plan view of the opposing major surface of the disk of FIG. 1.

One major surface of one embodiment of a sample processing disk 10 is depicted in FIG. 1. FIG. 2 is an enlarged cross-sectional view of one fluid structure in the sample processing disk 10. FIG. 3 depicts the opposing major surface 14 of the sample processing disk 10. It may be preferred that the sample processing disks of the present invention have a generally flat, disc-like shape, with two major sides 12 and 14 (side 12 seen in FIG. 1 and side 14 seen in FIG. 2). The thickness, of the sample processing disk 10 may vary depending on a variety of factors (e.g., the size of the features on the sample processing disk, etc.). In FIGS. 1-3, the features depicted in solid lines are formed on or into the visible side of the sample processing disk 10, while the features in broken lines are formed on or into the hidden or opposing side of the sample processing disk 10. It will be understood that the exact construction and location of the various features may change in different sample processing devices.

The sample processing disk 10 includes a plurality of fluid structures, with each fluid structures including an input well 20 and a process chamber 30. One or more delivery channels are provided to connect the input wells 20 to the process chambers 30. In the embodiment of FIGS. 1-3, each of the input wells 20 is connected to only one of the process chambers 30. It should, however, be understood that a single input well 20 could be connected to two or more process chambers 30 by any suitable arrangement of delivery channels.

Furthermore, it should be understood that within a given fluid structure on a sample processing disk of the present invention, multiple process chambers may be provided in a sequential relationship separated by valves, or other fluid control structures. Examples of some such fluid structures with multiple process chambers connected to each other may be seen in, e.g., U.S. Pat. No. 6,734,401 titled ENHANCED SAMPLE PROCESSING DEVICES SYSTEMS AND METHODS (Bedingham et al.).

The term "process chamber" as used herein should not be construed as limiting the chamber to one in which a process (e.g., PCR, Sanger sequencing, etc.) is performed. Rather, a process chamber as used herein may include, e.g., a chamber in which materials are loaded for subsequent delivery to another process chamber as the sample processing device if rotated, a chamber in which the product of a process is collected, a chamber in which materials are filtered, etc.

The disk 10 is formed by a central body 50 that includes a first major surface 52 and a second major surface 54 on the opposite side of the body 50. Although the body 50 is depicted a single, unitary article, it should be understood that it could alternatively be constructed of multiple elements attached together to form the desired structure. It may be preferred, however, that the body 50 be manufactured of a molded polymeric material. Further, it may be preferred that the body 50 be opaque to any electromagnetic radiation delivered into the process chambers 30 (for excitation, heating, etc.) or emitted from materials located in the process chambers 30. Such opacity in the body 50 may reduce the likelihood of, e.g., cross-talk between different process chambers 30 (or other features provided in the disks 10).

The features of the different fluid structures may preferably be formed by depressions, voids, raised structures, etc. that are formed on, into, and/or through the body 50. In such a construction, the features of the fluid structures may be defined at least in part by covers that may preferably be attached to the major surfaces 52 and 54 of the body 50. In other words, without covers defining the features of the fluid structures, the features would be open to atmosphere, allowing, potentially, for leaking and spillage of materials.

It may be preferred that at least one of the sides of the disk 10 present a surface that is complementary to a base plate or thermal structure apparatus as described in, e.g., U.S. Pat. No. 6,734,401 titled ENHANCED SAMPLE PROCESSING DEVICES SYSTEMS AND METHODS (Bedingham et al.) or U.S. patent application Ser. No. 11/174,757, titled SAMPLE PROCESSING DEVICE COMPRESSION SYSTEMS AND METHODS, filed on even date herewith. In some embodiments, it may be preferred that at least one of the major sides of the disks of the present invention present a flat surface.

In the disk 10 depicted in FIGS. 1-3, the input wells 20 are defined by voids that extend through the major surface 52 and 54 of the body 50. The input well 20 is defined on the bottom side (i.e., on major surface 54) by a central cover 60 that is attached to the surface 54 of the body 50. The input well 20 may preferably include an opening 22 on the upper side of the disk 10. The opening 22 in the depicted embodiment may preferably include a chamfer to assist in insertion of, e.g., a pipette or other sample delivery device into the input well 20.

It may be preferred that the opening 22 into the input well 20 be closed by an input well seal 24 attached over the opening 22. The input well seal 24 may preferably be attached to the disk over the opening 22 using, e.g., adhesives, heat sealing, etc. as discussed herein. Seal 24 may be attached over the openings 22 before the input wells 20 are loaded with sample materials to, e.g., prevent contamination of the input well 20 during shipping, handling, etc. Alternatively, the seal 24 may be attached after loading the input well 20 with sample material. In some instances, seals may be used before and after loading the input wells 20.

Although the seal 24 is depicted as a sheet of material, it should be understood that seals used to close input wells 20 may be provided in any suitable form, e.g., as plugs, caps, etc. It may be preferred that a single unitary seal be provided to close all of the input wells on a given disk or that a single unitary seal be used to seal only some of the input wells on a given disk. In another alternative, each seal 24 may be used to close only one input well 20.

Other features that may be included in connection with the input wells in the sample processing disks of the present invention are, e.g., the positioning of the input wells 20 within raised ribs 26 that may preferably be provided in the body 50. As seen in, e.g., FIG. 2, the raised rib 26 extends above the major surface 52 of the body surrounding the rib 26. One potential advantage of locating the input wells 20 in a raised structure on the disk 10 may be an increase in the volume of the input well 20 (as compared to an input well occupying the same amount of surface area on the disk 10 but limited to the volume between the major surfaces 52 and 54).

Another potential advantage of locating multiple input wells 20 in the raised ribs 26 that extend above the surface 54 of the body 50 may be an increase in the structural rigidity of central portion of the disk 10. That increased rigidity in the central portion of the disk may be useful alone, i.e., some disks according to the present invention may include raised structures on one side while presenting a flat surface on the opposing side. The location of the input wells on such a disk may not be in the raised structures where the increased volume that could be provided is not needed. Using such ribs or other raised structures can limit distortion or bending of the disk during storage, sample loading, etc.

In the depicted sample processing disk 10, the input well 20 in each of the fluid structures is connected to a process chamber 30 by a delivery channel that is a combination of an inner channel 42, a via 44 formed through the body 50, and an outer channel 46. The inner channel 42 extends from the input well 20 to the via 44 and is preferably defined in part by a groove or depression formed into major surface 54 of the body 50. The via 44 is preferably defined in part by a void that extends through both major surfaces 52 and 54 of the body 50.

The inner channel 42 and the end of the via 44 proximate major surface 54 are both also defined in part by a central cover 60 attached to the major surface 54 of the body 50. In the depicted embodiment, the central cover 60 includes an inner edge 62 around the spindle opening 56 formed in the body 50 and an outer edge 64 that preferably extends past the via 44 such that the central cover 60 can preferably define the boundary of the input well 20, the inner channel 42, and the via 44 on the major surface 54 of the body 50.

The outer channel 46 is preferably formed by a groove or depression in the surface 52 of the body 50 and extends from the via 44 to the process chamber 30. The outer channel 46 and end of the via 44 proximate the major surface 52 are preferably both defined by a cover 70 attached to the major surface 52 of the body 50. In the depicted embodiment, the cover 70 preferably includes an inner edge 72 that is located between the via 44 and the input well 20 and an outer edge 74 that is preferably located radially outward from the process chamber 30 such that it can define the boundaries of the fluid features as seen in, e.g., FIG. 2.

The process chamber 30 is also preferably sealed by a cover 80 attached to the surface 54 of the body 50 in which the void forming the process chamber 30 is located. The cover 80 preferably includes an inner edge 82 located between the via 44 and the process chamber 30 and an outer edge 84 that is preferably located radially outward from the process chamber 30 such that it can provide the desired sealing function. It may be preferred that the outer edge 64 of the central cover 60 and the inner edge 82 of the second annular cover 80 define a junction that is located radially outside of the annular ring defined by the vias 44 of the plurality of fluid structures as seen in FIG. 2.

With reference primarily to FIGS. 1 and 2, the arrangement of various features on the sample processing disk 10 may be described. It may be preferred that, in general, the disks of the present invention be provided as circular articles with selected features of the disks arranged in circular arrays on the circular disks. It should be understood, however, that disks of the present invention need not be perfectly circular and may, in some instances, be provided in shapes that are not circles. For example, the disks may take shapes such as, e.g., pentagons, hexagons, octagons, etc. Similarly, the features arranged in circular arrays on the exemplary disk 10 may be provided in arrays having similar non-circular shapes.

In the exemplary sample processing disk 10, it may be preferred that the vias 44 and the process chambers 30 be arranged such that they define circular arrays or annular rings on the disk 10. Such an arrangement may allow for the use of a central cover 60 that includes an outer edge 64 that is generally circular in shape, with the outer edge 64 of the central cover 60 located between the via 44 and the process chamber 30. Concentric circular arrays of vias 44 and process chambers 30 may allow for the use of a cover 70 on the surface 52 of the body 50 that includes an inner edge 72 and an outer edge 74 that are both circular, with the cover 70 being provided in the form of an annular ring on the surface 52 of the body 50. The concentric circular arrays of the vias 44 and the process chambers 30 may also allow for the use of a cover 80 on the surface 54 of the body 50 that includes a circular inner edge 82 located between the vias 44 and the process chambers 30 and a circular outer edge 84 located radially outward of the process chambers 30. Other complementary shapes for the arrays of vias 44 and process arrays 30 may, of course, be used with the covers 60, 70 and 80 taking the appropriate shapes to seal the different features as discussed herein.

Although the cover 80 used to define the process chambers 30 on the surface 54 of the body 50 may preferably be limited to the annular ring outside of central cover 60, it should be understood that this may not be required. For example, it may be possible to use a single unitary cover on the surface 54 of the body to seal the input wells 20, inner channel 42, via 44 and process chamber 30. One potential advantage of the multiple covers 60 and 70 attached to the surface 54 of the body 50 is, however, that the metallic layer included in cover 80 may be limited to the area occupied by the process chambers 30. As such, the transfer of thermal energy towards the central part of the body 50 may be limited if the central cover 60 is manufactured from materials that are not as thermally conductive as metals.

The body 50 and the different covers 60, 70, and 80 used to seal the fluid structures in the disks of the present invention may be manufactured of any suitable material or materials. Examples of suitable materials may include, e.g., polymeric materials (e.g., polypropylene, polyester, polycarbonate, polyethylene, etc.), metals (e.g., metal foils), etc. The covers may preferably, but not necessarily, be provided in generally flat sheet-like pieces of, e.g., metal foil, polymeric material, multi-layer composite, etc. It may be preferred that the materials selected for the body and the covers of the disks exhibit good water barrier properties.

It may be preferred that at least one of the covers 70 and 80 sealing the process chambers 30 be constructed of a material or materials that substantially transmit electromagnetic energy of selected wavelengths. For example, it may be preferred that one of the covers 70 and 80 be constructed of a material that allows for visual or machine monitoring of fluorescence or color changes within the process chambers 30.

It may also be preferred that at least one of the covers 70 and 80 include a metallic layer, e.g., a metallic foil. If provided as a metallic foil, the cover may preferably include a passivation layer on the surface that faces the interior of the fluid structures to prevent contact between the sample materials and the metal. Such a passivation layer may also function as a bonding structure where it can be used in, e.g., hot melt bonding of polymers. As an alternative to a separate passivation layer, any adhesive layer used to attach the cover to the body 50 may also serve as a passivation layer to prevent contact between the sample materials and any metals in the cover.

In the illustrative embodiment of the sample processing disk 10 depicted in FIGS. 1-3, the cover 70 may preferably be manufactured of a polymeric film (e.g., polypropylene) while the cover 80 on the opposite side of the process chamber 30 may preferably include a metallic layer (e.g., a metallic foil layer of aluminum, etc.). In such an embodiment, the cover 70 preferably transmits electromagnetic radiation of selected wavelengths, e.g., the visible spectrum, the ultraviolet spectrum, etc. into and/or out of the process chambers 30 while the metallic layer of cover 80 facilitates thermal energy transfer into and/or out of the process chambers 30 using thermal structures/surfaces as described in, e.g., U.S. Pat. No. 6,734,401 titled ENHANCED SAMPLE PROCESSING DEVICES SYSTEMS AND METHODS (Bedingham et al.) or U.S. patent application Ser. No. 11/174,757, titled SAMPLE PROCESSING DEVICE COMPRESSION SYSTEMS AND METHODS, filed on even date herewith.

It may be preferred that the outer cover 80 located within or defining the annular processing ring be relatively thermally conductive (e.g., metallic, etc.) in comparison to the central cover 60, which may preferably be a relatively nonconductive material (such as plastic, etc.). Such a combination may be useful for rapid heating and/or cooling of sample materials in the process chambers 30, while limiting thermal transfer into or out of the inner region of the disk, i.e., the region within the annular processing ring defined by the process chambers 30. While such an arrangement may enhance thermal control within the annular processing ring, it may be difficult to position, attach, etc. the central cover 60 and outer cover 80 such that a leakproof junction between two such dissimilar covers is formed. That is, if a continuous channel underlay both covers, the junction between the covers could render the disk susceptible to leakage of fluid through the junction during the process of moving fluids through the channels. Use of a via 44 to move the channel from one side of the disk body 50 to the other provides the opportunity to avoid such a junction. As a result, the delivery channels do not run directly underneath a cover junction. In such an embodiment, the junction lies outward of the array of vias 44 and inward from the array of process chambers 30 within the annular processing ring.

The covers 60, 70, and 80 may be attached to the surfaces 52 and 54 of the body 50 by any suitable technique or techniques, e.g., melt bonding, adhesives, combinations of melt bonding and adhesives, etc. If melt bonded, it may be preferred that both the cover and the surface to which it is attached include, e.g., polypropylene or some other melt bondable material, to facilitate melt bonding. It may, however, be preferred that the covers be attached using pressure sensitive adhesive. The pressure sensitive adhesive may be provided in the form of a layer of pressure sensitive adhesive that may preferably be provided as a continuous, unbroken layer between the cover and the opposing surface 52 or 54. Examples of some potentially suitable attachment techniques, adhesives, etc. may be described in, e.g., U.S. Pat. No. 6,734,401 titled ENHANCED SAMPLE PROCESSING DEVICES SYSTEMS AND METHODS (Bedingham et al.) and U.S. Patent Application Publication No. US 2002/0064885 titled SAMPLE PROCESSING DEVICES.

Pressure sensitive adhesives typically exhibit viscoelastic properties that may preferably allow for some movement of the covers relative to the underlying body to which the covers are attached. The movement may be the result of deformation of the annular processing ring to, e.g., conform to the shape of a thermal transfer structure as described in U.S. patent application Ser. No. 11/174,757, titled SAMPLE PROCESSING DEVICE COMPRESSION SYSTEMS AND METHODS, filed on even date herewith. The relative movement may also be the result of different thermal expansion rates between the covers and the body. Regardless of the cause of the relative movement between covers and bodies in the disks of the present invention, it may be preferred that the viscoelastic properties of the pressure sensitive adhesive allow the process chambers and other fluid features of the fluid structures to preferably retain their fluidic integrity (i.e., they do not leak) in spite of the deformation.

Many different pressure sensitive adhesives may potentially be used in connection with the present invention. One well-known technique for identifying pressure sensitive adhesives is the Dahlquist criterion. This criterion defines a pressure sensitive adhesive as an adhesive having a 1 second creep compliance of greater than $1 \times 10^{-6}$ $cm^2$/dyne as described in *Handbook of Pressure Sensitive Adhesive Technology*, Donatas Satas (Ed.), $2^{nd}$ Edition, p. 172, Van Nostrand Reinhold, New York, N.Y., 1989. Alternatively, since modulus is, to a first approximation, the inverse of creep compliance, pressure sensitive adhesives may be defined as adhesives having a Young's modulus of less than $1\times10^6$ dynes/$cm^2$. Another well known technique for identifying a pressure sensitive adhesive is that it is aggressively and permanently tacky at room temperature and firmly adheres to a variety of dissimilar surfaces upon mere contact without the need of more than finger or hand pressure, and which may be removed from smooth surfaces without leaving a residue as described in *Test Methods for Pressure Sensitive Adhesive Tapes*, Pressure Sensitive Tape Council, (1996). Another suitable definition of a suitable pressure sensitive adhesive is that it preferably has a room temperature storage modulus within the area defined by the following points as plotted on a graph of modulus versus frequency at 25° C.: a range of moduli from approximately $2\times10^5$ to $4\times10^5$ dynes/$cm^2$ at a frequency of approximately 0.1 radian/second (0.017 Hz), and a range of moduli from approximately $2\times10^6$ to $8\times10^6$ dynes/$cm^2$ at a frequency of approximately 100 radians/second (17 Hz) (for example see FIGS. 8-16 on p. 173 of *Handbook of Pressure Sensitive Adhesive Technology*, Donatas Satas (Ed.), $2^{nd}$ Edition, Van Nostrand Rheinhold, New York, 1989). Any of these methods of identifying a pressure sensitive adhesive may be used to identify potentially suitable pressure sensitive adhesives for use in the methods of the present invention.

It may be preferred that the pressure sensitive adhesives used in connection with the sample processing disks of the present invention include materials which ensure that the properties of the pressure sensitive adhesive are not adversely affected by water. For example, the pressure sensitive adhesive will preferably not lose adhesion, lose cohesive strength, soften, swell, or opacify in response to exposure to water during sample loading and processing. Also, the pressure sensitive adhesive preferably do not contain any components which may be extracted into water during sample processing, thus possibly compromising the device performance.

In view of these considerations, it may be preferred that the pressure sensitive adhesive be composed of hydrophobic materials. As such, it may be preferred that the pressure sensitive adhesive be composed of silicone materials. That is, the pressure sensitive adhesive may be selected from the class of silicone pressure sensitive adhesive materials, based on the combination of silicone polymers and tackifying resins, as described in, for example, "Silicone Pressure Sensitive Adhesives", *Handbook of Pressure Sensitive Adhesive Technology*, $3^{rd}$ Edition, pp. 508-517. Silicone pressure sensitive adhesives are known for their hydrophobicity, their ability to withstand high temperatures, and their ability to bond to a variety of dissimilar surfaces.

The composition of the pressure sensitive adhesives is preferably chosen to meet the stringent requirements of the present invention. Some suitable compositions may be described in International Publication WO 00/68336 titled SILICONE ADHESIVES, ARTICLES, AND METHODS (Ko et al.).

Other suitable compositions may be based on the family of silicone-polyurea based pressure sensitive adhesives. Such compositions are described in U.S. Pat. No. 5,461,134 (Leir et al.); U.S. Pat. No. 6,007,914 (Joseph et al.); International Publication No. WO 96/35458 (and its related U.S. patent application Ser. No. 08/427,788 (filed Apr. 25, 1995); U.S. Ser. No. 08/428,934 (filed Apr. 25, 1995); U.S. Ser. No. 08/588,157 (filed Jan. 17, 1996); and U.S. Ser. No. 08/588,159 (filed Jan. 17, 1996); International Publication No. WO 96/34028 (and its related U.S. patent application Ser. No. 08/428,299 (filed Apr. 25, 1995); U.S. Ser. No. 08/428,936 (filed Apr. 25, 1995); U.S. Ser. No. 08/569,909 (filed Dec. 8, 1995); and U.S. Ser. No. 08/569,877 (filed Dec. 8, 1995)); and International Publication No. WO 96/34029 (and its related U.S. patent application Ser. No. 08/428,735 (filed Apr. 25, 1995) and U.S. Ser. No. 08/591,205 (filed Jan. 17, 1996)).

Such pressure sensitive adhesives are based on the combination of silicone-polyurea polymers and tackifying agents. Tackifying agents can be chosen from within the categories of functional (reactive) and nonfunctional tackifiers as desired. The level of tackifying agent or agents can be varied as desired so as to impart the desired tackiness to the adhesive composition. For example, it may be preferred that the pressure sensitive adhesive composition be a tackified polydiorganosiloxane oligurea segmented copolymer including (a) soft polydiorganosiloxane units, hard polyisocyanate residue units, wherein the polyisocyanate residue is the polyisocyanate minus the —NCO groups, optionally, soft and/or hard organic polyamine units, wherein the residues of isocyanate units and amine units are connected by urea linkages; and (b) one or more tackifying agents (e.g., silicate resins, etc.).

Furthermore, the pressure sensitive layer of the sample processing disks of the present invention can be a single pressure sensitive adhesive or a combination or blend of two or more pressure sensitive adhesives. The pressure sensitive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. In order to achieve maximum bond fidelity and, if desired, to serve as a passivation layer, the adhesive layer may preferably be continuous and free from pinholes or porosity.

Even though the sample processing devices may be manufactured with a pressure sensitive adhesive to connect the various components, e.g., covers, bodies, etc., together, it may be preferable to increase adhesion between the components by laminating them together under elevated heat and/or pressure to ensure firm attachment of the components.

It may be preferred to use adhesives that exhibit pressure sensitive properties. Such adhesives may be more amenable to high volume production of sample processing devices since they typically do not involve the high temperature bonding processes used in melt bonding, nor do they present the handling problems inherent in use of liquid adhesives, solvent bonding, ultrasonic bonding, and the like.

The adhesives are preferably selected for their ability to, e.g., adhere well to materials used to construct the covers and bodies to which the covers are attached, maintain adhesion during high and low temperature storage (e.g., about −80° C. to about 150° C.) while providing an effective barrier to sample evaporation, resist dissolution in water, react with the components of the sample materials used in the disks, etc. Thus, the type of adhesive may not be critical as long as it does not interfere (e.g., bind DNA, dissolve, etc.) with any processes performed in the sample processing disk 10. Preferred adhesives may include those typically used on cover films of analytical devices in which biological reactions are carried out. These include poly-alpha olefins and silicones, for example, as described in International Publication Nos. WO 00/45180 (Ko et al.) and WO 00/68336 (Ko et al.).

Furthermore, the pressure sensitive adhesive layer of the sample processing disks of the present invention can be a single adhesive or a combination or blend of two or more adhesives. The adhesive layers may result from solvent coating, screen printing, roller printing, melt extrusion coating, melt spraying, stripe coating, or laminating processes, for example. An adhesive layer can have a wide variety of thicknesses as long as it meets exhibits the above characteristics and properties. In order to achieve maximum bond fidelity and, if desired, to serve as a passivation layer, the adhesive layer may preferably be continuous and free from pinholes or porosity.

Even though the sample processing disks may be manufactured with a pressure sensitive adhesive to connect the various components, e.g., sides, together, it may be preferable to increase adhesion between the components by laminating them together under elevated heat and/or pressure to ensure firm attachment.

Figure 4:
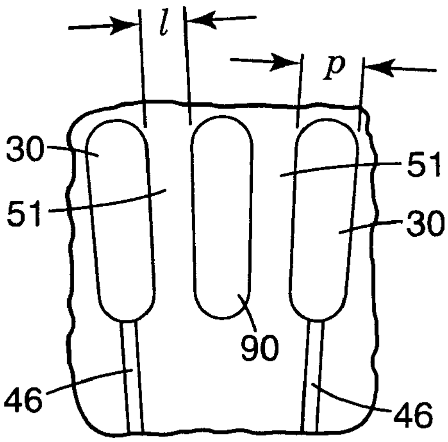
FIG. 4 is an enlarged view of a portion of a circular array of process chambers in one embodiment of a sample processing disk of the present invention.

An optional feature that may be provided in the sample processing disks of the present invention is depicted in FIG. 4 which is an enlarged view of a portion of the annular processing ring containing the array of process chambers 30 on the disk 10. The process chambers 30 are in fluid communication with input wells through channels 46 as discussed herein. Where the process chambers 30 are provided in a circular array as depicted in FIGS. 1 and 3, it may be preferred that the process chambers 30 form a compliant annular processing ring that is adapted to conform to the shape of an underlying thermal transfer surface when the sample processing disk is forced against the thermal transfer surface. Compliance is preferably achieved with some deformation of the annular processing ring while maintaining the fluidic integrity of the process chambers 30 (i.e., without causing leaks). Such a compliant annular processing ring may be useful when used in connection with the methods and systems described in, e.g., U.S. patent application Ser. No. 11/174,757, titled SAMPLE PROCESSING DEVICE COMPRESSION SYSTEMS AND METHODS, filed on even date herewith.

Annular processing rings formed as composite structures using components attached to each other with viscoelastic pressure sensitive adhesives may, as described herein, exhibit compliance in response to forces applied to the sample processing disk. Compliance of annular processing rings in sample processing disks of the present invention may alternatively be provided by, e.g., locating the process chambers 30 in an (e.g., circular) array within the annular processing ring in which a majority of the area is occupied by voids in the body 50. As discussed herein, e.g., the process chambers 30 themselves may preferably be formed by voids in the body 50 that are closed by the covers attached to the body 50. To improve compliance or flexibility of the annular ring occupied by the process chambers 30, it may be preferred that the voids of the process chambers 30 occupy 50% or more of the volume of the body 50 located within the annular processing ring defined by the process chambers 30.

Compliance of the annular processing rings in sample processing disks of the present invention may preferably be provided by a combination of an annular processing ring formed as a composite structure using viscoelastic pressure sensitive adhesive and voids located within the annular processing ring. Such a combination may provide more compliance than either approach taken alone.

Referring again FIG. 4, another optional feature depicted is an orphan chamber 90 located between the process chambers 30. Where the area occupied by the process chambers 30 is lower, the addition of orphan chambers in the annular processing ring may be used to improve compliance and flexibility. Although the orphan chamber 90 has the same general shape as the process chambers 30 as depicted in FIG. 4, orphan chambers may or may not have the same shape as the process chambers in sample processing disks of the present invention.

As used in connection with the present invention, an orphan chamber is a chamber that is formed by a void through the body or by a depression formed into one on the major surfaces of the body. When a cover is placed over the void or depression, the volume of the orphan chamber 90 is defined, but the volume of the orphan chamber is not connected to any other features in a fluid structure by a delivery channel as are process chambers.

Such orphan chambers may, for example, improve flexibility of the disk within the annular processing ring by reducing the amount of body material within the annular processing ring. Orphan chambers may also improve thermal isolation between process chambers located on opposite sides of an orphan chamber. They may also reduce the thermal mass of the disk within the annular processing ring by providing an air-filled chamber with a lower thermal mass than if the disk were solid. Reduced thermal mass may increase the rate at which sample materials within the process chambers 30 can be heated or cooled.

In embodiments of sample processing disks that include orphan chambers 90 in addition to process chambers 30 within the annular processing ring, it may be preferred that the voids of the process chambers 30 and the orphan chambers located within the annular processing ring together occupy 50% or more of the volume of the body 50 located within the annular processing ring.

Another manner of characterizing the amount of material present in the annular processing ring containing the process chambers 30 is based on the relative width of the process chambers 30 as compared to the width of the land 51 separating adjacent process chambers 30 in the circular array. For example, it may be preferred that, proximate a radial midpoint within the annular ring defined by the process chambers 30, adjacent process chambers 30 are separated from each other by a land area 51 having a width (l) that is equal to or less than the width (p) of each process chamber 30 of the adjacent process chambers 30 on each side of the land area 51. In some embodiments, it may be preferred that, proximate a radial midpoint within the annular ring defined by the process chambers 30, adjacent process chambers 30 be separated from each other by a land area 51 having a land width (l) that is 50% or less of the width (p) of each process chamber 30 of the adjacent process chambers 30 on each side of the land area 51.

Another optional feature depicted in the sample processing disk 10 of FIGS. 1-3 (particularly FIG. 2) is the outer flange that includes an upper portion 92 extending above the side 12 of the disk 10 and a lower portion 94 that extends below the side 14 of the disk 10.

The flange may provide a variety of functions. For example, it may be used as a convenient location for grasping the disk 10 that may be particularly useful in robotic transfer systems. The flange may also provide a convenient location for identification marks such as, e.g., bar codes, or items such as RFID tags that may be used to identify the disk 10. The flange may also prevent the features on the sides 12 and 14 of the disk 10 from contacting surfaces on which the disks 10 are placed. It may be preferred that one portion of the flange (the lower portion 94 in the depicted embodiment) be flared outward or otherwise constructed in a manner that provides for stacking of multiple disks 10 by providing a surface 96 against which the flange of a disk 10 located below the disk 10 of FIG. 2 can rest. If used for stacking, it may be preferred that the upper portion 92 extend above the surface 52 of the body 50 farther than any of the features provided on that side 12 of the disk 10.

The flange may also serve to improve the structural integrity of the disk 10 by behaving structurally as a hoop to unify the outer portion of the process chambers (and orphan chambers (if any) in the annular processing ring. The rigidity of the outer flange may be adjusted to allow the annular processing ring to conform to imperfections in a thermal transfer surface, etc.

Figure 5:
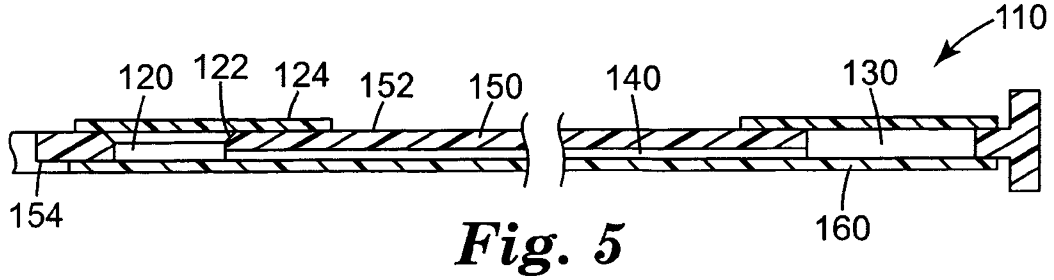
FIG. 5 is a cross-sectional view of a portion of another exemplary embodiment of a microfluidic sample processing disk according to the present invention.

An alternative embodiment of a sample processing disk 110 is depicted in connection with FIG. 5 in which a disk 110 includes features similar in many respects to the those found in the disk 10 of FIGS. 1-3. One difference is, however, that the input wells 120 are connected to the process chambers 130 using a delivery channel 140 that is located on only one side of the body 150 (surface 154 of body 150 in FIG. 5). As a result, the cover 160 used on surface 154 may extend over all of the input well 120, the delivery channel 140 and the process chamber 130. In addition, a via is not required to redirect the flow from the surface 154 to the surface 152.

Another difference depicted in connection with disk 110 is that the input well 120 includes an opening 122 that is closed by a seal 124 applied directly to surface 152 of body 150. In other words, input well 120 is not located within a raised structure as seen in disk 10 of FIGS. 1-3.

Among the other features that may be provided in connection with sample processing disks of the present invention, FIGS. 1 and 3 also depict examples of some potentially advantageous arrangements for the input wells 20 and delivery channel paths extending from the input wells 20 to the process chambers 30. It may be advantageous to rotate the sample processing disks of the present invention to, e.g., move sample material from the input well 20 in a fluid structure to the process chamber 30.

For example, the disk 10 may preferably be rotated about an axis of rotation 11 depicted as a point in FIGS. 1 and 3. It may be preferred that the axis of rotation 11 be generally perpendicular to the opposing sides 12 and 14 of the disk 10, although that arrangement may not be required. The disk 10 may preferably include a spindle opening 56 proximate the center of the body 50 that is adapted to mate with a spindle (not shown) used to rotate the disk 10 about axis 11. The axis of rotation 11 may also preferably serve to define the center of the circular arrays in which the vias 44 and process chambers 30 may preferably be arranged as discussed herein. In general, the process chambers 30 are located radially outward from the input wells 20 to facilitate movement of sample materials from the input wells 20 to the process chambers 30 when the disk 10 is rotated about axis 11.

As discussed herein, it may be preferred that the sample processing disks of the present invention include an annular processing ring that exhibits compliance to improve thermal control over materials in the process chambers on the disks. One example of how the compliant annular processing rings may be used is depicted in connection with FIG. 6. A portion of a sample processing disk 210 according to the present invention is depicted in FIG. 6 in contact with a shaped transfer surface 206 formed on a thermal structure 208.

Thermal structures and their transfer surfaces may be described in more detail in, e.g., U.S. patent application Ser. No. 11/174,757, titled SAMPLE PROCESSING DEVICE COMPRESSION SYSTEMS AND METHODS, filed on even date herewith. Briefly, however, the temperature of the thermal structure 208 may preferably be controlled by any suitable technique, with the transfer surface 206 facilitating transfer of thermal energy into or out of the thermal structure 208 to control the temperature of items such as sample processing disks placed in contact with the transfer surface 206.

Where the item to be thermally controlled is a sample processing disk, enhancement in thermal energy transfer between the thermal structure and the disk may be achieved by conforming the disk to the shape of the transfer surface 206. Where only a portion of the disk, e.g., an annular processing ring is in contact with the transfer surface, it may be preferred that only that portion of the disk 210 be deformed such that it conforms to the shape of the transfer surface 206.

Figure 6:
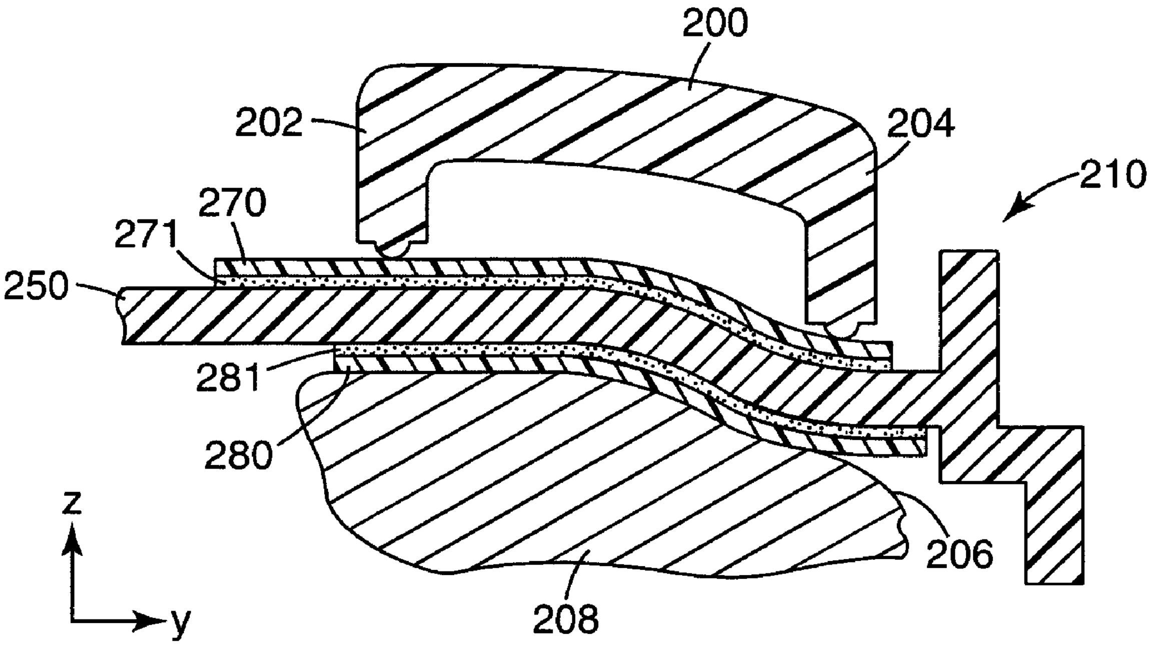
FIG. 6 is an enlarged cross-sectional view of a sample processing disk deflected to conform to a thermal transfer surface.

FIG. 6 depicts one example of such a situation in which a sample processing disk 210 includes a body 250 having covers 270 and 280 attached thereto using adhesive (preferably pressure sensitive adhesive) layers 271 and 281 respectively. The covers 270 and 280 may preferably be generally limited to the area of the annular processing ring as described herein. The use of viscoelastic pressure sensitive adhesive for layers 271 and 281 may improve compliance of the annular processing ring of the disk 210 as is also described herein.

By deforming the disk 210 to conform to the shape of the transfer surface 206 as depicted, thermal coupling efficiency between the thermal structure 208 and the sample processing disk 210 may be improved. Such deformation of the sample processing disk 210 may be useful in promoting contact even if the surface of the sample processing disk 210 facing the transfer surface 206 or the transfer surface 206 itself include irregularities that could otherwise interfere with uniform contact in the absence of deformation.

To further promote deformation of the sample processing disk 210 to conform to the shape of the transfer surface 206, it may be preferred to include compression rings 202 and 204 in the cover 200 used to provide a compressive force on the sample processing disk 210 in connection with the transfer surface 206, such that the rings 202 and 204 contact the sample processing disk 210—essentially spanning the annular processing ring of the disk 210 that faces the transfer surface 206. By limiting contact between the cover 200 and the annular processing ring of the disk 210 to rings 202 and 204, enhanced thermal control may be achieved because less thermal energy will be transferred through the limited contact area between the cover 200 and the disk 210.

As seen in FIG. 6, deformation of the disk 210 may preferably involve deflection of the annular processing in a direction normal to the major surfaces of the disk 210, i.e., along the z-axis as depicted in FIG. 6 which can also be described as in a direction normal to the major surface of the disk.

As used herein and in the appended claims, the singular forms "a," "and," and "the" include plural referents unless the context clearly dictates otherwise. Thus, for example, reference to "a" or "the" component may include one or more of the components and equivalents thereof known to those skilled in the art.

All references and publications cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the claims provided below and equivalents thereof.

The invention claimed is:

1. A microfluidic sample processing disk comprising:

a body comprising first and second major surfaces;

a plurality of fluid structures, wherein each fluid structure of the plurality of fluid structures comprises:

an input well comprising an opening;

a process chamber located radially outward of the input well, wherein the process chamber comprises a void formed through the first and second major surfaces of the body; and a delivery channel connecting the input well to the process chamber, wherein the delivery channel comprises an inner channel formed in the second major surface of the body, an outer channel formed in the first major surface of the body, and a via formed through the first and second major surfaces of the body, wherein the via connects the inner channel to the outer channel;

wherein the vias and the process chambers of the plurality of fluid structures define annular rings on the body;

a first annular cover attached to the first major surface of the body, the first annular cover defining the vias, the outer channels, and the process chambers in connection with the first major surface of the body;

a second annular cover attached to the second major surface of the body, the second annular cover defining the process chambers of the plurality of fluid structures in connection with the second major surface of the body, wherein an inner edge of the second annular cover is located radially outward of the annular ring defined by the vias of the plurality of fluid structures; and a central cover attached to the second major surface of the body, the central cover defining the inner channels and the vias in connection with the second major surface of the body, wherein an outer edge of the central cover is located radially outward of the annular ring defined by the vias of the plurality of fluid structures.

2. A microfluidic sample processing disk according to claim 1, wherein the input wells of the plurality of fluid structures are located within raised structures extending above the first major surface of the body, wherein each raised structure of the plurality of raised structures comprises two or more of the input wells.

3. A microfluidic sample processing disk according to claim 2, wherein the inner channels extending from two or more input wells in each of the raised structures extend along lines that are not coincident with a radius defined by a center of the annular rings.

4. A microfluidic sample processing disk according to claim 1, wherein the outer edge of the central cover and the inner edge of the second annular cover define a junction located radially outside of the annular ring defined by the vias of the plurality of fluid structures.

5. A microfluidic sample processing disk according to claim 1, wherein the input wells comprise voids formed through the first and second major surfaces of the body, wherein the central cover defines ends of the input wells on the second major surface of the body.

6. A microfluidic sample processing disk according to claim 1, wherein the second annular cover comprises a metallic foil layer.

7. A microfluidic sample processing disk according to claim 1, wherein the first annular cover transmits electromagnetic radiation of selected wavelengths into and/or out of the process chambers of the plurality of fluid structures.

8. A microfluidic sample processing disk according to claim 1, wherein the first annular cover, the second annular cover, and the central cover are adhesively attached to the body using one or more pressure sensitive adhesives.

9. A microfluidic sample processing disk according to claim 1, wherein the process chambers of the plurality of fluid structures define an annular processing ring on the sample processing disk, wherein the process chambers occupy 50% or more of the volume of the body within the annular processing ring.

10. A microfluidic sample processing disk according to claim 1, wherein the process chambers of the plurality of fluid structures define an annular processing ring on the sample processing disk, and wherein one or more orphan chambers are located within the annular processing ring, wherein each orphan chamber is formed by a void or depression in the body and one or both of the first annular cover and the second annular cover.

11. A microfluidic sample processing disk according to claim 10, wherein the voids of the process chambers and the orphan chambers together occupy 50% or more of the volume of the body within the annular processing ring.

12. A microfluidic sample processing disk according to claim 1, further comprising an input well seal adapted to close the opening in the input well of each fluid structure of the plurality of fluid structures.

13. A microfluidic sample processing disk according to claim 12, wherein the input well seal is adhesively attached over the opening in the input well of each fluid structure of the plurality of fluid structures.

14. A microfluidic sample processing disk comprising:

a body comprising first and second major surfaces;

a plurality of fluid structures, wherein each fluid structure of the plurality of fluid structures comprises:

an input well comprising an opening;

a process chamber located radially outward of the input well, wherein the process chamber comprises a void formed through the first and second major surfaces of the body; and a delivery channel connecting the input well to the process chamber;

a first cover attached to the first major surface of the body with a pressure sensitive adhesive, the first cover defining a portion of the process chambers of the plurality of fluid structures in connection with the first major surface of the body;

a second cover attached to the second major surface of the body with a pressure sensitive adhesive, the second cover defining a portion of the process chambers of the plurality of fluid structures in connection with the second major surface of the body, wherein the second cover comprises an inner edge and an outer edge that is located radially outward of the inner edge;

wherein the process chambers of the plurality of fluid structures define an annular processing ring that comprises an inner edge and an outer edge located radially inward of a perimeter of the body, wherein the inner edge of the annular processing ring is located radially outward of the inner edge of the second cover.

15. A microfluidic sample processing disk according to claim 14, wherein the process chambers of the plurality of fluid structures occupy 50% or more of the volume of the body within the annular processing ring.

16. A microfluidic sample processing disk according to claim 14, wherein the second cover comprises a metallic layer.

17. A microfluidic sample processing disk according to claim 16, wherein the metallic layer is coextensive with the second cover.

18. A microfluidic sample processing disk according to claim 14, wherein the second cover comprises a metallic layer, and wherein the first cover comprises a polymeric layer that transmits electromagnetic energy of selected wavelengths into or out of the process chambers of the plurality of fluid structures.

19. A microfluidic sample processing disk according to claim 14, wherein the delivery channel comprises an inner channel formed in the second major surface of the body, an outer channel formed in the first major surface of the body, and a via formed through the first and second major surfaces of the body, wherein the via connects the inner channel to the outer channel and wherein the vias of the plurality of fluid structures define an annular array of vias on the body;

wherein the first cover defines a portion of the vias and the outer channels;

and wherein the microfluidic sample processing disk further comprises a central cover attached to the second major surface of the body, the central cover defining the inner channels and the vias in connection with the second major surface of the body, wherein an outer edge of the central cover is located radially outward of the annular array of vias.

20. A microfluidic sample processing disk according to claim 19, wherein the outer edge of the central cover is located radially inward of the inner edge of the second cover.

21. A microfluidic sample processing disk according to claim 19, wherein the outer edge of the central cover and the inner edge of the second cover define a junction located radially outside of the annular array of vias.

22. A microfluidic sample processing disk according to claim 14, wherein the input wells of the plurality of fluid structures are located within raised structures extending above the first major surface of the body, wherein each raised structure of the plurality of raised structures comprises two or more of the input wells.

23. A microfluidic sample processing disk according to claim 14, wherein the input wells comprise voids formed through the first and second major surfaces of the body, wherein the central cover defines ends of the input wells on the second major surface of the body.

24. A microfluidic sample processing disk according to claim 14, further comprising an input well seal adapted to close the opening in the input well of each fluid structure of the plurality of fluid structures.

25. A microfluidic sample processing disk according to claim 24, wherein the input well seal is attached over the opening in the input well of each fluid structure of the plurality of fluid structures with a pressure sensitive adhesive.

26. A microfluidic sample processing disk comprising:

a body that comprises first and second major surfaces;

an annular processing ring comprising a plurality of process chambers formed in the body, each process chamber of the plurality of process chambers defining an independent volume for containing sample material;

an annular metallic layer located within the annular processing ring, wherein the annular metallic layer is proximate the first surface of the body, wherein the plurality of process chambers are located between the annular metallic layer and the second major surface of the body;

a plurality of channels formed in the body, wherein each channel of the plurality of channels is in fluid communication with at least one process chamber of the plurality of process chambers;

wherein the annular processing ring comprises a compliant structure in which the independent volumes of the plurality of process chambers maintain fluidic integrity when a portion of the annular processing ring is deflected in a direction normal to the first and second major surfaces of the body.

27. A microfluidic sample processing disk according to claim 26, wherein the plurality of process chambers occupy 50% or more of the volume of the body within the annular processing ring.

28. A microfluidic sample processing disk according to claim 26, wherein one or more orphan chambers are located within the annular processing ring, wherein each orphan chamber comprises a void or depression in the body.

29. A microfluidic sample processing disk according to claim 28, wherein the plurality of process chambers and the orphan chambers together occupy 50% or more of the volume of the body within the annular processing ring.

30. A microfluidic sample processing disk according to claim 26, wherein the annular metallic layer is attached to the first surface of the body with a pressure sensitive adhesive.

31. A microfluidic sample processing disk according to claim 26, wherein the annular processing ring comprises an annular transmissive cover attached to the second surface of the body with a pressure sensitive adhesive, wherein the annular metallic layer is attached to the first surface of the body with a pressure sensitive adhesive, and wherein each process chamber of the plurality of process chambers is defined by a void formed through the first and second major surfaces of the body, a portion of the annular transmissive cover and a portion of the annular metallic cover.

* * * * *

UNITED STATES PATENT AND TRADEMARK OFFICE

CERTIFICATE OF CORRECTION

PATENT NO. : 7,763,210 B2
APPLICATION NO. : 11/174680
DATED : July 27, 2010
INVENTOR(S) : William Bedingham It is certified that error appears in the above-identified patent and that said Letters Patent is hereby corrected as shown below:

On the Title Page:

Page 3
Column 2, Line 13 under Other Publications Delete "Minature;" and insert -- Miniature; --, therefor.

In the Specifications:

Column 7
Line 41, Delete "thickness," and insert -- thickness --, therefor.

Column 12
Line 51, Delete "Rheinhold," and insert -- Reinhold, --, therefor.

Signed and Sealed this

Twelfth Day of October, 2010

David J. Kappos
*Director of the United States Patent and Trademark Office*